United States Patent [19]

Pike

[11] Patent Number: 4,582,631

[45] Date of Patent: Apr. 15, 1986

[54] HIGH FLASH POINT FUEL CONTROL CALIBRATION FLUID

[75] Inventor: Roscoe A. Pike, Simsbury, Conn.

[73] Assignee: United Technologies Corporation, Hartford, Conn.

[21] Appl. No.: 526,834

[22] Filed: Aug. 26, 1983

[51] Int. Cl.$^4$ .................. C09K 3/00; G01N 31/00; C10L 1/00; C10L 1/02

[52] U.S. Cl. .................... 252/408.1; 44/50; 44/56

[58] Field of Search .......... 252/408.1; 44/50, 56, 44/66

[56] References Cited

U.S. PATENT DOCUMENTS

| | | | |
|---|---|---|---|
| 1,420,622 | 6/1922 | Charbonneaux | 44/55 |
| 3,907,516 | 9/1975 | Biasotti | 44/66 X |
| 4,033,897 | 7/1977 | Banard | 436/8 X |
| 4,067,699 | 1/1978 | Lukasiewicz | 44/66 |
| 4,146,454 | 3/1979 | Haber | 424/12 X |
| 4,147,643 | 4/1979 | Pindar | 44/78 X |
| 4,256,596 | 3/1981 | Cohen | 44/78 X |
| 4,404,109 | 9/1983 | Tellier et al. | 252/312 X |

*Primary Examiner*—Christine M. Nucker
*Assistant Examiner*—Catherine S. Kilby
*Attorney, Agent, or Firm*—Alan C. Cohen

[57] ABSTRACT

The present invention is directed toward novel high flash point fluids useful in the calibration of jet engine fuel controls. These compositions comprise about 70 weight percent to about 90 weight percent of dodecane and about 10 weight percent to about 30 weight percent of a material selected from the group consisting of organic esters, ethers and acids. Said fluids have flash points which are greater than 170° F. (76.7° C.) making calibration of the fuel controls safer.

10 Claims, No Drawings

HIGH FLASH POINT FUEL CONTROL CALIBRATION FLUID

DESCRIPTION

1. Technical Field

The present invention relates to a high flash point, calibraton fluid useful in the calibration of jet engine fuel controls.

2. Background Art

The construction and design of present day jet engine fuel controls is a highly technical engineering task. These fuel controls are sophisticated metering devices which vary the fuel consumption in jet engines according to the different demands on the engine. Should these devices fail to perform properly, the result may be engine failure which may prove disastrous to the aircraft. The fuel control, due to its critical role in flight, undergoes extensive testing to determine its flight worthiness, and performance characteristics.

One important test is to stimulate the conditions under which the fuel control will operate in flight and monitor its performance. Typically, this is done on a test stand. The test stand is a complex arrangement of gauges, dials and hoses which allows the operator to attach the fuel control to the stand and monitor the flow of a fluid through the fuel control. These test stands are generally capable of varying the conditions under which the fuel control will operate. These conditions include operating the stand at temperatures from about −65° F. (−53.8° C.) to about 300° F. (148.9° C.) and pressures as high as 1500 psi.

In simulating the fuel control's behavior during calibration, a test fluid is used in place of the jet fuel which would be used in actual flight. The test fluid is used in these tests principally because of the safety hazards associated with working with the jet fuel, due in large part to its flammable nature as evidenced by its very low flash point (0° F. (−17.8° C.)). A substitute fluid which is currently being used is known by its military designation as Mil-C-7024B or Stoddard Solvent. The key in developing this substitute fluid was to locate a material which had a significantly higher flash point than the jet fuel, but which had the same or essentially the same key physical properties required for the calibration process. The key physical properties which are crucial to the calibration process are density, vapor pressure, viscosity and to a certain extent, thermal conductivity. The Stoddard Solvent may be characterized as a straight-run petroleum naphtha fraction containing principally aliphatic hydrocarbons having a density of 0.76 g/cc, vapor pressure of 2 psi maximum, viscosity of 1.12 centistokes and a thermal conductivity of 0.079 BTU/ft$^2$/in/°F./ft. The flash point of this material is 107° F. (41.6° C.), a considerable improvement over jet fuel.

Since the development of the Stoddard Solvent calibraton fluid, the National Electrical Code has been upgraded placing more restrictive requirements on equipment which is being used in the presence of low flash point fluids. The upgraded code requires the use of special equipment, i.e. fittings, tubings and switch boxes, when the fluid used in the system has a flash point below 150° F. Such precautions, although necessary in light of the safety hazards, adds significantly to the cost of construction of one of these test stands. A more significant safety advancement would be to develop a substitute fluid having a flash point greater than 150° F., preferably significantly higher. Such a substitute fluid would be required to have physical properties, i.e. density, viscosity, thermal conductivity, very close to that of Stoddard Solvent. Ideally, the substitute fluid would also have a low vapor pressure to reduce cavitation during testing, and must be compatible with the materials, i.e seals, etc. which are present in both the test stand and the fuel control.

Therefore, what is needed in the art is a substitute fluid for use in jet engine fuel control test stands which has similar physical properties to Stoddard Solvent but with a considerably higher flash point.

DISCLOSURE OF INVENTION

The present invention is directed toward relatively high flash point compositions of matter which are useful in the calibration of jet engine fuel controls. The compositions are comprised of about 70 to about 90 weight percent dodecane and about 10 to about 30 weight percent of an organic ester, ether, alcohol or acid. The principal function of the organic ester, ether or acid is to act as a density modifier for the dodecane. These modifiers may be characterized as having high flash points (greater than 140° F.) densities greater than 0.80 g/cc and containing at least eight carbon atoms. These modifiers must also be miscible with dodecane and compatible with the materials in the fuel controls and calibration test stand. The resulting compositions are characterized by a high flash point (greater than 170° F.), a density of 0.76 g/cc, a vapor pressure below 2 psi and a viscosity of from about 1.5 centistokes (cs) to about 1.85 centistokes at 100° F. These fluids, due to these higher flash points, will reduce the cost of calibration test stand construction and will also reduce cavitation of the fluid during calibration.

BEST MODE FOR CARRYING OUT THE INVENTION

The high temperature flash point calibration fluids of the present invention are solutions of dodecane ($C_{12}H_{26}$) and an organic ester, ether, alcohol or acid, density modifier. These fluids range in composition from about 70 to about 90 weight percent of dodecane with the balance being at least one of a number of long chain, high molecular weight organic esters, ethers or acids. Table I contains a list of a number of suitable density modifiers which have been used to formulate calibrating fluids having the requisite density, flash point and viscosity. One surprising feature of these mixtures is that the viscosity of the final solution is remarkably different than that which would be expected for any combination of dodecane (1.676 cs) and one of the modifiers. This unique feature allows for the addition of a greater quantity of a modifying material while the resulting fluid viscosity remains within the useful range.

TABLE I

| | Density | Viscosity, cs | Flash Point |
|---|---|---|---|
| Dibutylcarbitol (diethylene glycol dibutyl ether) | 0.885 | 2.39 | 245° F. (118° C.) |
| 2-ethylhexanoic acid | 0.91 | 7.73 | 260° F. (126° C.) |
| 2-octanol | .82 | | 140° F. (60° C.) |
| dioctyl phthalate (di-2-ethylhexyl phthalate) | .99 | 81.4 | 425° F. (218° C.) |

TABLE I-continued

| | Density | Viscosity, cs | Flash Point |
|---|---|---|---|
| didecyl phthalate | .97 | 113.2 | 445° F. (229° C.) |

Table II contains six high flash point fluids which were formulated and tested to determine the proper makeup and the final physical properties of the fluids. As can be seen, the fluids contain about 70 weight percent of dodecane with the balance being one of the organic modifiers. All of the fluids have the density of 0.76 g/cc while maintaining a flash point greater than 173° F.

TABLE II

| | Density g/cc | Viscosity, cs 100° F. | Flash Pt °F. |
|---|---|---|---|
| dodecane/dibutylcarbitol (80/20) | 0.76 | 1.52 | 181 |
| dodecane/2-ethylhexanoic acid (90/10) | 0.76 | 1.60 | 183 |
| dodecane/2-octanol (70/30) | 0.76 | 1.85 | 173 |
| dodecane/dioctyl phthalate (90/10) | 0.76 | 1.69 | 181 |
| dodecane/didecyl phthalate (90/10) | 0.76 | 1.72 | 182 |
| Stoddard Solvent | 0.76 | 1.12 | 107 |

Although any of these fluids would be useful in calibrating jet engine fuel controls, the preferred fluid is comprised of about 90 weight percent dodecane and about 10 weight percent dioctyl phthalate. The principal reasons for selecting this fluid as the preferred embodiment results from the lower cost of the modifier and the lack of a disagreeable odor which is present in a number of the other fluids. The fluid was prepared by mixing an appropriate amount of technical grade dodecane with an appropriate amount of analytical grade dioctyl phthalate. The resulting solution was then used in a jet fuel control calibration system where it performed satisfactorily. Table III lists the important physical properties of this preferred fluid in comparison to the prior fluids used in the calibration process.

TABLE III

| Properties | Dodecane 90%/ Dioctyl Phthalate 10% | Stoddard Solvent | JP-4 |
|---|---|---|---|
| Density, g/cc | 0.76 | 0.76 | 0.76 |
| Viscosity, cs | 1.69(100° F.) | 1.12 (100° F.) | 1.14(60° F.) |
| Flash point, °F. | 181 | 107 | 0 |
| Thermal conductivity, BTU/hr/ft$^2$/°F. | 0.0895 | 0.081 | — |
| Vapor pressure, psi | 0.2 | 1-2 | 2.5 |

Although this particular fluid was made using both analytical and technical grades of material, there does not appear to be any reason why less pure materials, i.e. commercial grade, would not prove to be just as satisfactory.

The physical properties of the solutions prepared using this invention make them ideal candidates for replacing the Stoddard Solvent used in calibrating jet engine fuel controls. The much higher flash points reduce the safety hazard accompanying Stoddard Solvent. In addition, since these solutions have flash points considerably above those required for Class I applications, the test stands for testing the fuel controls will not require such stringent, heavy duty electrical hardware, reducing the cost of construction for these stands. The business communities which build or overhaul jet engines will find that these solutions will reduce the test stand costs and more importantly will make the testing procedure safer.

It should be understood that the invention is not limited to the particular embodiments shown and described herein, but that various changes and modifictions may be made without departing from the spirit and scope of this novel concept as defined by the following claims.

I claim:

1. A high flash point fluid particularly adapted for use in the calibration of jet engine fuel metering devices comprising about 90 weight percent dodecane and about 10 weight percent of dioctyl phthalate, said fluid having a flash point above 170° F. (76.7° C.) and a density of 0.76 g/cc.

2. A high flash point fluid particularly adapted for use in the calibration of jet engine fuel metering devices comprising about 80 weight percent dodecane and about 20 weight percent of diglycidyl dibutyl ether, said fluid having a flash point above 170° F. (76.7° C.) and a density of 0.76 g/cc.

3. A high flash point fluid particularly adapted for use in the calibration of jet engine fuel metering devices comprising about 90 weight percent of dodecane and about 10 weight percent of 2-ethyl hexanoic acid, said fluid having a flash point above 170° F. (76.6° C.) and a density of 0.76 g/cc.

4. A high flash point fluid particularly adapted for use in the calibration of jet engine fuel meterine devices comprising about 70 weight percent of dodecane and about 30 weight percent of 2-octanol, said fluid having a flash point above 170° F. (76.6° C.) and a density of 0.76 g/cc.

5. A high flash point fluid particularly adapted for use in the calibration of jet engine fuel metering devices comprising about 90 weight percent of dodecane and about 10 weight percent of didecyl phthalate, said fluid having a flash point above 170° F. (76.6° C.) and a density of 0.76 g/cc.

6. A method of calibrating a jet fuel metering device comprising:
attaching the fuel control to a test stand,
flowing a calibration fluid through the fuel metering device at temperatures from about −65° F. (−53.8° C.) to about 300° F. (148.9° C.) and pressure up to about 1500 psi,
measuring the flow of said fluid through the fuel control under these conditions of temperature and pressure wherein the improvement comprises:
the use of a calibrating fluid containing about 90 weight percent of dodecane and about 10 weight percent of dioctyl phthalate, wherein said fluid has a flash point greater than 170° F. (76.6° C.) and a density of 0.76 g/cc.

7. A method of calibrating a jet fuel metering device comprising:
attaching the fuel control to a test stand,
flowing a calibration fluid through the fuel metering device at temperatures from about −65° F. (−53.8° C.) to about 300° F. (148.9° C.) and pressure up to about 1500 psi,
measuring the flow of said fluid through the fuel control under these conditions of temperature and pressure wherein the improvement comprises:
the use of a calibrating fluid containing about 80 weight percent of dodecane and about 20 weight percent of diglycidyl dibutyl ether, said fluid having a flash point above 170° F. (76.7° C.) and a density of 0.76 g/cc.

8. A method of calibrating a jet fuel metering device comprising:

attaching the fuel control to a test stand, flowing a calibration fluid through the fuel metering device at temperatures from about −65° F. (−53.8° C.) to about 300° F. (148.9° C.) and pressure up to about 1500 psi, measuring the flow of said fluid through the fuel control under these conditions of temperature and pressure wherein the improvement comprises:

the use of a calibrating fluid containing about 90 weight percent of dodecane and about 10 weight percent of 2-ethyl hexanoic acid, said fluid having a flash point above 170° F. (76.6° C.) and a density of about 0.76 g/cc.

9. A method of calibrating a jet fuel metering device comprising:

attaching the fuel control to a test stand, flowing a calibration fluid through the fuel metering device at temperatures from about −65° F. (−53.8° C.) to about 300° F. (148.9° C.) and pressure up to about 1500 psi, measuring the flow of said fluid through the fuel control under these conditions of temperature and pressure wherein the improvement comprises:

the use of a calibrating fluid containing about 70 weight percent of dodecane and about 30 weight percent of 2-octanol, said fluid having a flash point above 170° F. (76.6° C.) and a density of 0.76 g/cc.

10. A method of calibrating a jet fuel metering device comprising:

attaching the fuel control to a test stand, flowing a calibration fluid through the fuel metering device at temperatures from about −65° F. (−53.8° C.) to about 300° F. (148.9° C.) and pressure up to about 1500 psi, measuring the flow of said fluid through the fuel control under these conditions of temperature and pressure wherein the improvement comprises:

the use of a calibrating fluid containing about 90 weight percent of dodecane and about 10 weight percent of didecyl phthalate, said fluid having a flash point above 170° F. (76.6° C.) and a density of 0.76 g/cc.

* * * * *